(12) United States Patent
Kangas

(10) Patent No.: US 8,795,704 B2
(45) Date of Patent: *Aug. 5, 2014

(54) MEDICAL DEVICES HAVING FLUORINE-CONTAINING POLYMER COATINGS WITH IMPROVED ADHESION

(75) Inventor: Steve Kangas, Woodbury, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1239 days.

This patent is subject to a terminal disclaimer.

(21) Appl. No.: 12/544,537

(22) Filed: Aug. 20, 2009

(65) Prior Publication Data

US 2010/0057189 A1    Mar. 4, 2010

Related U.S. Application Data

(60) Provisional application No. 61/092,360, filed on Aug. 27, 2008.

(51) Int. Cl.
*A61F 2/00* (2006.01)

(52) U.S. Cl.
USPC .......................................................... 424/423

(58) Field of Classification Search
None
See application file for complete search history.

(56) References Cited

U.S. PATENT DOCUMENTS

| | | | | |
|---|---|---|---|---|
| 5,726,250 | A * | 3/1998 | Zajaczkowski | 525/296 |
| 6,545,097 | B2 | 4/2003 | Pinchuk et al. | |
| 7,329,413 | B1 | 2/2008 | Pacetti et al. | |
| 8,168,213 | B2 * | 5/2012 | Kangas et al. | 424/423 |
| 2004/0063805 | A1 * | 4/2004 | Pacetti et al. | 523/113 |
| 2005/0106204 | A1 | 5/2005 | Hossainy et al. | |
| 2006/0093771 | A1 * | 5/2006 | Rypacek et al. | 428/36.91 |
| 2006/0134165 | A1 | 6/2006 | Pacetti | |
| 2006/0246209 | A1 * | 11/2006 | McNiven et al. | 427/2.1 |
| 2006/0280770 | A1 | 12/2006 | Hossainy et al. | |
| 2008/0014241 | A1 | 1/2008 | DesNoyer et al. | |
| 2008/0286333 | A1 | 11/2008 | Kangas et al. | |
| 2009/0326647 | A1 | 12/2009 | Quillin | |

FOREIGN PATENT DOCUMENTS

| | | |
|---|---|---|
| WO | 2008006912 A2 | 1/2008 |
| WO | 2008027107 A2 | 3/2008 |

OTHER PUBLICATIONS

T. Kowalewski et al., "Complex nanostructured materials from segmented copolymers prepared by ATRP", Eur. Phys. J. E, vol. 10, (2003), pp. 5-16.
B. Reeves, "Recent Advances in Living Free Radical Polymerization", Nov. 20, 2001, University of Florida, pp. 1-14.
J. Pyun et al., "Synthesis of Nanocomposite Organic/Inorganic Hybrid Materials Using Controlled/"Living" Radical Polymerization", Chem. Mater., vol. 13, (2001), pp. 3436-3448.

* cited by examiner

*Primary Examiner* — Carlos Azpuru
*Assistant Examiner* — Casey Hagopian
(74) *Attorney, Agent, or Firm* — Fish & Richardson P.C.

(57) ABSTRACT

According to an aspect of the present invention, medical devices are provided which include a metallic substrate and a polymeric region disposed over and in contact with the metallic substrate. The polymeric region includes (a) a fluorine-containing polymer that contains at least one type of fluorine-containing monomer selected from a vinylidene fluoride monomer, a hexafluoropropylene monomer, and a combination thereof, and (b) an adhesion promoting copolymer that contains (i) at least one type of first monomer that covalently or non-covalently bonds with the metallic substrate and (ii) at least one type of second monomer selected from acrylate monomers, methacrylate monomers, fluorine-containing monomers, and combinations thereof.

25 Claims, 2 Drawing Sheets

US 8,795,704 B2

MEDICAL DEVICES HAVING FLUORINE-CONTAINING POLYMER COATINGS WITH IMPROVED ADHESION

RELATED APPLICATIONS

This application claims priority from U.S. provisional application 61/092,360, filed Aug. 27, 2008, which is incorporated by reference herein in its entirety.

FIELD OF THE INVENTION

The present invention relates generally to medical devices, and more particularly to implantable or insertable medical devices having fluorine-containing polymer coatings with improved adhesion.

BACKGROUND OF THE INVENTION

Numerous polymer-based medical devices have been developed for implantation or insertion into the body. For example, in recent years, drug eluting coronary stents, which are commercially available from Boston Scientific Corp. (TAXUS and PROMUS), Johnson & Johnson (CYPHER) and others, have been employed for maintaining vessel patency. These existing products are based on metallic expandable stents with polymer coatings, which release anti-restenotic drugs at a controlled rate and total dose. Specific examples of polymers for drug eluting polymer coatings include various copolymers such as poly(ethylene-co-vinyl acetate), poly(styrene-b-isobutylene-b-styrene) triblock copolymers (SIBS), described, for instance, in U.S. Pat. No. 6,545,097 to Pinchuk et al., and poly(vinylidene fluoride-co-hexafluoropropylene) (PVDF-HFP), described, for instance, in Pub. No. 2005/0106204 to Hossainy et al.

In one process, the outer surface of a stainless steel coronary stent is sprayed first with a solution that contains poly (n-butyl methacrylate) as an adhesion promoting coating, and then with a solution that contains PVDF-HFP and everolimus as a drug eluting coating. See, e.g., Pub. No. 2005/0106204 to Hossainy et al. The solutions are sprayed on the outside of the stent, and to some degree, through the stent struts. The stent struts are ultimately encapsulated with the two coatings due to a combination of outside spraying and through-strut spraying combined with flow of the solution around the stent struts. The net result is that the spray process results in a conformal coating.

The result of such a process is schematically illustrated in FIGS. 1A and 1B. FIG. 1A shows a stent 100 which contains a number of interconnected struts 100s. FIG. 1B is a cross-section taken along line b-b of strut 100s of stent 100 of FIG. 1A, and shows a stainless steel stent substrate 110, an adhesion promoting coating 120, and a drug eluting coating 130. Because the drug eluting coating 130 encapsulates the adhesion promoting coating 120 and the substrate 110, the coating 120 does not need to be particularly efficacious at promoting adhesion between the coating 130 and substrate 110, so long as the coating 130 has good mechanical integrity.

SUMMARY OF THE INVENTION

According to an aspect of the present invention, medical devices are provided which comprise a metallic substrate and polymeric region disposed over and in contact with the metallic substrate. The polymeric region comprises a fluorine-containing polymer that comprises a fluorine-containing monomer selected from a vinylidene fluoride monomer, a hexafluoropropylene monomer, and a combination thereof. The polymeric region also comprises an adhesion promoting copolymer that comprises (i) a first monomer that covalently or non-covalently bonds with the metallic substrate and (ii) a second monomer selected from acrylate monomers, methacrylate monomers, fluorine-containing monomers, and a combination thereof.

In certain embodiments, the polymeric region further comprises a drug.

An advantage of the present invention is medical devices are provided with polymeric regions which have improved adhesion to metallic substrates.

These and many other aspects, embodiments and advantages of the present invention will become immediately apparent to those of ordinary skill in the art upon review of the Detailed Description and Claims to follow.

DETAILED DESCRIPTION OF THE INVENTION

Figure 1A:
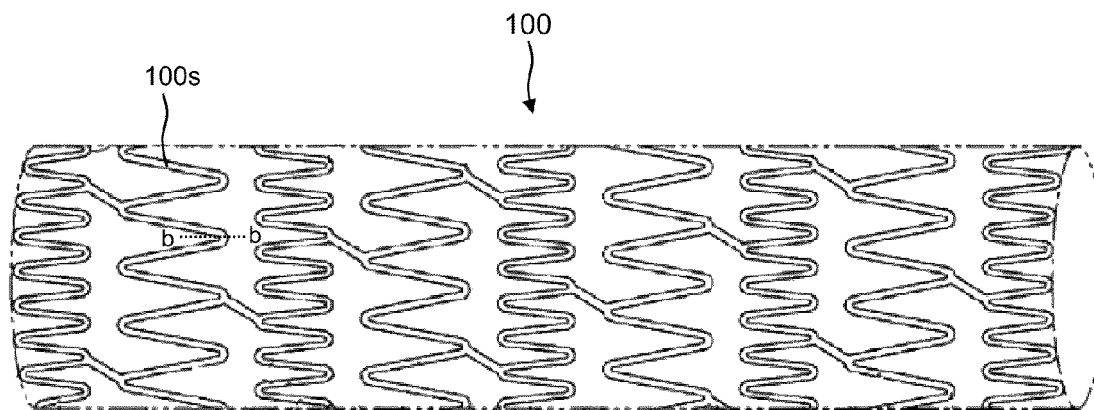
FIG. 1A is an illustration of a stent in accordance with the prior art.
Figure 1B:
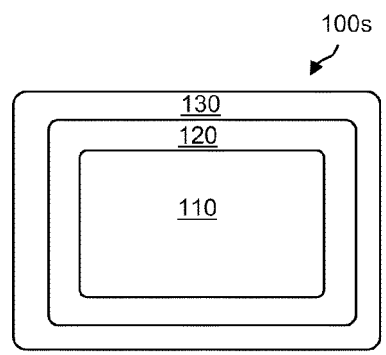
FIG. 1B is a cross-section taken along line b-b of FIG. 1A.

A more complete understanding of the present invention is available by reference to the following detailed description of numerous aspects and embodiments of the invention. The detailed description of the invention which follows is intended to illustrate but not limit the invention.

According to an aspect of the present invention, medical devices are provided which comprise a metallic substrate and a polymeric region disposed over and in contact with the metallic substrate. The polymeric region comprises (a) a fluorine-containing polymer that contains at least one type of fluorine-containing monomer selected from a vinylidene fluoride monomer, a hexafluoropropylene monomer, and a combination thereof, (b) an adhesion promoting copolymer and (c) optionally, a drug. The adhesion promoting copolymer contains (i) at least one type of monomer that covalently or non-covalently bonds with the metallic substrate and (ii) at least one type of monomer selected from acrylate monomers, methacrylate monomers, fluorine-containing monomers, and a combination thereof.

In certain embodiments, the polymeric regions of the invention comprise a polymeric layer disposed over and in contact with the metallic substrate, which polymeric layer comprises the fluorine-containing polymer, the adhesion promoting copolymer and, optionally, the drug.

In certain embodiments, the polymeric regions of the invention comprise (a) an adhesion promoting layer comprising the adhesion promoting copolymer disposed over and in contact with the metallic substrate, and (b) a polymeric layer, which comprises the fluorine-containing polymer and, optionally, the drug, disposed over and in contact with the adhesion promoting layer.

As used herein, a "polymeric region" is a three-dimensional entity that contains polymers, for example, from 50 wt % or less to 75 wt % to 90 wt % to 95 wt % to 97.5 wt % to 99 wt % or more of one or more types of polymers. As used herein, a "polymeric region" can comprise two or more adjacent polymeric layers.

As used herein, a "polymeric layer" is a layer that contains polymers. As used herein a "layer" of a given material is a region of that material whose thickness is small compared to its length and width (i.e., 25% or less, more typically 10% or less). Layers in accordance with the present invention can be disposed over all or only a portion of an underlying metallic substrate, depending on the application. Layers can be provided over an underlying substrate at a variety of locations and in a variety of shapes (e.g., in the form of a series of rectangles, stripes, or any other continuous or non-continuous pattern). As used herein a layer need not be planar, for example, taking on the contours of an underlying substrate. Terms such as "coating," "film" and "layer" may be used herein interchangeably herein.

As used herein, a "drug release layer" or "drug eluting layer" is polymeric layer that contains a drug and releases it into the body.

As used herein, an "adhesion promoting layer" is a polymeric layer that comprises an adhesion promoting copolymer.

As used herein, an "adhesion promoting copolymer" is (a) a copolymer that, when included in a polymeric layer with one or more other polymers, provides improved adhesion of the polymeric layer to an adjacent metallic substrate, relative to such adhesion when the adhesion promoting copolymer is not included in the polymeric layer or (b) a copolymer that, when provided in the form of a first polymeric layer between a metallic substrate and a second polymeric layer, provides improved adhesion between the second polymeric layer and the metallic substrate, relative to such adhesion in the absence of the first polymeric layer.

Adhesion may be measured, for example, by ASTM Test Method D1876-01 Standard Test Method for Peel Resistance of Adhesives (T-Peel Test) or similar test methods or by measuring 180 degree peel of the coating from the substrate (similar to ASTM peel adhesion 3330/D3330M-04).

As used herein a "metallic substrate" is one containing metals, for example, from 50 wt % or less to 75 wt % to 90 wt % to 95 wt % to 97.5 wt % to 99 wt % or more of one or more metals.

Specific examples of metallic substrates may be selected, for example, from substantially pure metals such as gold, silver, iron, nickel, copper, aluminum, niobium, platinum, palladium, iridium, osmium, rhodium, titanium, tantalum, tungsten, ruthenium, zinc and magnesium, among others, and alloys such as those comprising iron and chromium (e.g., stainless steels, including platinum-enriched radiopaque stainless steel), niobium alloys, tantalum alloys, titanium alloys, including alloys comprising nickel and titanium (e.g., Nitinol), alloys comprising cobalt and chromium, including alloys that comprise cobalt, chromium and iron (e.g., elgiloy alloys), alloys comprising nickel, cobalt and chromium (e.g., MP 35N), alloys comprising cobalt, chromium, tungsten and nickel (e.g., L605), alloys comprising nickel and chromium (e.g., inconel alloys), and biodisintegrable alloys including alloys of magnesium, zinc and/or iron (and their alloys with combinations of one another and with Ce, Ca, Zr, La and Li), among others.

As used herein, "polymers" are molecules containing multiple copies (e.g., from 5 to 10 to 25 to 50 to 100 to 250 to 500 to 1000 or more copies) of one or more types of constitutional units, commonly referred to as monomers. As used herein, the term "monomers" may refer to the free monomers and those that are incorporated into polymers, with the distinction being clear from the context in which the term is used.

Polymers may take on a number of configurations, which may be selected, for example, from linear, branched and cyclic configurations, among others. Branched configurations include star-shaped configurations (e.g., configurations in which three or more chains emanate from a single branch point), comb configurations (e.g., configurations having a main chain and a plurality of side chains, also referred to as "graft" configurations), dendritic configurations (e.g., arborescent and hyperbranched polymers), networked configurations (e.g., crosslinked configurations) and so forth.

As used herein, "homopolymers" are polymers that contain multiple copies of a single monomer. "Copolymers" are polymers that contain multiple copies of at least two dissimilar monomers, examples of which include random, statistical, gradient, periodic (e.g., alternating) and block copolymers.

Medical devices in accordance with the invention vary widely. Examples include implantable or insertable medical devices, for example, for example, stents (including coronary vascular stents, peripheral vascular stents, cerebral, urethral, ureteral, biliary, tracheal, gastrointestinal and esophageal stents), stent coverings, stent grafts, vascular grafts, abdominal aortic aneurysm (AAA) devices (e.g., AAA stents, AAA grafts, etc.), vascular access ports, dialysis ports, catheters (e.g., urological catheters or vascular catheters such as balloon catheters and various central venous catheters), guide wires, balloons, filters (e.g., vena cava filters and mesh filters for distil protection devices), embolization devices including cerebral aneurysm filler coils (including Guglielmi detachable coils and metal coils), embolic agents, septal defect closure devices, drug depots that are adapted for placement in an artery for treatment of the portion of the artery distal to the device, myocardial plugs, pacemakers, leads including pacemaker leads, defibrillation leads and coils, neurostimulation leads such as spinal cord stimulation leads, deep brain stimulation leads, peripheral nerve stimulation leads, cochlear implant leads and retinal implant leads, ventricular assist devices including left ventricular assist hearts and pumps, total artificial hearts, shunts, valves including heart valves and vascular valves, anastomosis clips and rings, tissue bulking devices, suture anchors, tissue staples and ligating clips at surgical sites, cannulae, metal wire ligatures, tacks for ligament attachment and meniscal repair, joint prostheses, spinal discs and nuclei, orthopedic prosthesis such as bone grafts, bone plates, fins and fusion devices, orthopedic fixation devices such as interference screws in the ankle, knee, and hand areas, rods and pins for fracture fixation, screws and plates for craniomaxillofacial repair, dental implants, or other devices that are implanted or inserted into the body.

As previously indicated, in some aspects, the present invention is directed to medical devices which comprise a metallic substrate and a polymeric region disposed over and in contact with the metallic substrate. The polymeric region comprises a fluorine-containing polymer that comprises a fluorine-containing monomer selected from a vinylidene fluoride monomer, a hexafluoropropylene monomer, and a combination thereof. The polymeric region also comprises an adhesion promoting copolymer that comprises (i) a first monomer that covalently or non-covalently bonds with the metallic substrate and (ii) a second monomer selected from acrylate monomers, methacrylate monomers, fluorine-containing monomers, and a combination thereof.

Without wishing to be bound by theory, it is believed that the first monomer within the adhesion promoting copolymer promotes good adhesion of the polymeric region to the substrate, whereas the second monomer within the adhesion promoting copolymer promotes good interaction between the adhesion promoting copolymer and the fluorine-containing polymer within the polymeric region.

As indicated above, in certain embodiments, polymeric regions in accordance with the invention comprise a polymeric layer disposed over and in contact with a metallic substrate, which polymeric layer comprises a fluorine-containing polymer, an adhesion promoting copolymer and, optionally, a drug.

Figure 2A:
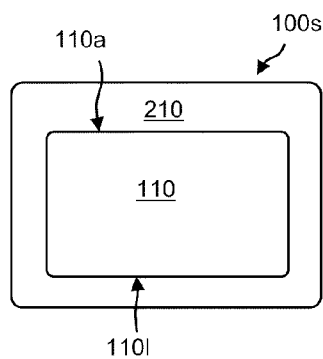
FIGS. 2A to 2C are schematic cross-sections of coated stent struts in accordance with various embodiments of the invention.

A specific embodiment of this aspect of the invention is illustrated in FIG. 2A, which is a cross-sectional view of a stent strut 110s, for example, one corresponding to a stent design like that of FIG. 1A (albeit with a different coating scheme, as described below). The stent strut 110s includes a metallic stent substrate 110 over which is disposed a polymeric region, in particular, an adhesion promoting, drug release layer 210 that contains (i) a fluorine-containing polymer, (ii) an adhesion promoting polymer and (iii) an antirestenotic drug.

While it is desirable to provide the abluminal (vessel contacting) surface of the stent substrate 100a with a polymeric coating that that is capable of releasing an anti-restenotic drug, such a drug may not be equally desirable on the luminal (blood contacting) surface of the stent substrate 110l. Moreover, the presence of a polymeric layer on the luminal surface may not be needed for purposes of promoting biocompatibility, as various stent substrate materials, including stainless steel, are known to support endothelial cell growth.

Figure 2B:
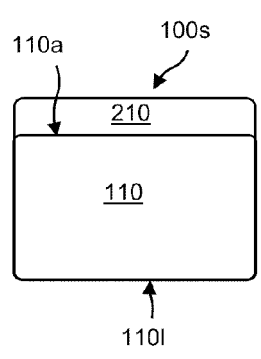

In this regard, another specific embodiment of the invention is illustrated in FIG. 2B, which like FIG. 2A is a cross-sectional view of a stent strut 110s that includes a metallic stent substrate 110 over which is disposed an adhesion promoting, drug release layer 210 containing (i) a fluorine-containing polymer, (ii) an adhesion promoting polymer and (iii) a drug. Unlike FIG. 2A, however, the layer 210 of FIG. 2B is applied only to the abluminal surface 110a of the stent substrate 110. Such a layer 210 may be created, for example, by coating a tubular stent precursor (e.g., a tube) with the layer 210 prior to removing material (e.g., by cutting, punching, etc.) in order to form the apertures (and thus the struts) of the stent, or by any other suitable methodology (e.g., transfer coating to a previously formed stent).

Figure 2C:
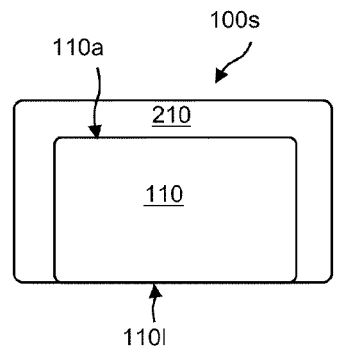

Yet another specific embodiment is illustrated in FIG. 2C, which, like FIGS. 2A and 2B, is a cross-sectional view of a stent strut 110s that includes a metallic stent substrate 110 over which is disposed an adhesion promoting, drug release layer 210 containing (i) a fluorine-containing polymer, (ii) an adhesion promoting polymer and (iii) a drug. Unlike FIGS. 2A and 2B, however, the layer 210 in FIG. 2C is applied to the abluminal surface 110a of the stent substrate 110, as well as to the sides of the stent substrate 110 between the abluminal surface 110a and the luminal surface 110l. The luminal surface of the stent 110l is not coated. Such a layer 210 may be created, for example, by masking the inner luminal surface of the stent 110l during deposition of the layer 210 (e.g., by placing it on a mandrel), by removing polymeric material from the inner luminal surface of the stent 110l after creating the layer 210, or by any other suitable methodology.

The embodiments of FIGS. 2B and 2C are more demanding from an adhesion standpoint than the embodiment of FIG. 2A, because the coating 210 does not surround the stent substrate 110 as it does in FIG. 2A.

As previously noted, in certain embodiments, polymeric regions in accordance with the present invention comprise (a) an adhesion promoting layer comprising an adhesion promoting copolymer disposed over and in contact with a metallic substrate, and (b) a polymeric layer comprising a fluorine-containing polymer (and, optionally, a drug) disposed over and in contact with the adhesion promoting layer. As also previously noted, the adhesion promoting copolymer comprises (i) a first monomer that covalently or non-covalently bonds with the metallic substrate and (ii) a second monomer selected from acrylate monomers, methacrylate monomers, fluorine-containing monomers, and a combination thereof.

Without wishing to be bound by theory, it is believed that the first monomer within the adhesion promoting copolymer promotes good adhesion of the adhesion promoting layer to the substrate, whereas the second monomer within the adhesion promoting copolymer promotes good interaction between the adhesion promoting layer and the overlying polymeric layer that comprises the fluorine-containing polymer.

Figure 3A:
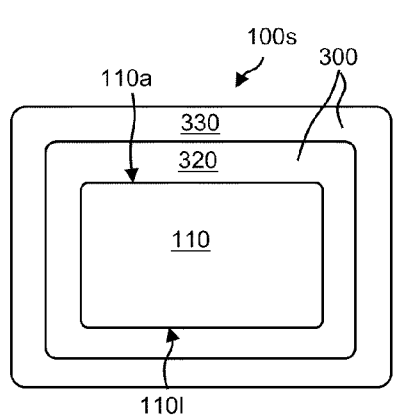
FIGS. 3A to 3C are schematic cross-sections of coated stent struts in accordance with various additional embodiments of the invention.

A specific embodiment of this aspect of the invention is illustrated in FIG. 3A, which is a cross-sectional view of a stent strut 110s, for example, one corresponding to a stent design like that of FIG. 1A (albeit with a different coating scheme as described below). The stent strut 110s of FIG. 3A includes a metallic stent substrate 110 and a polymeric region 300 that includes (a) an adhesion promoting layer 320 that contains an adhesion promoting copolymer and is disposed over and in contact with the metallic stent substrate 110 as well as (b) a polymeric layer 330 that contains a fluorine-containing polymer (and, optionally, a drug), disposed over and in contact with the adhesion promoting layer 320.

Figure 3B:
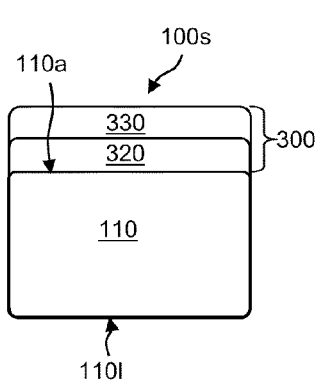

Another specific embodiment is illustrated in FIG. 3B, which is a cross-sectional view of a stent strut 110s that includes a stent substrate 110 and a polymeric region 300. The polymeric region 300 includes (a) an adhesion promoting layer 320, which contains an adhesion promoting copolymer and is disposed over and in contact with the stent substrate 110, and (b) a polymeric layer 330, which contains a fluorine-containing polymer (and, optionally, a drug), disposed over and in contact with the adhesion promoting layer 320. Unlike FIG. 3A, the adhesion promoting layer 320 and the polymeric layer 330 of FIG. 3B are applied to only the abluminal surface 110a of the stent substrate 110 in this embodiment. Such a structure may be created, for example, by coating a tubular stent precursor with the adhesion promoting layer 320 and the polymeric layer 330, followed by removing material (e.g., by cutting, punching, etc.) to form the apertures (and thus the struts) of the stent, or by any other suitable methodology (e.g., transfer coating to a previously formed stent).

Figure 3C:
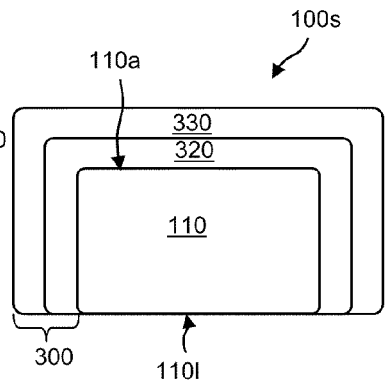

Yet another specific embodiment is illustrated in FIG. 3C, which is a cross-sectional view of a stent strut 110s that includes a stent substrate 110 and a polymeric region 300. The polymeric region 300 includes (a) an adhesion promoting layer 320, which contains an adhesion promoting copolymer and is disposed over and in contact with the stent substrate 110, and (b) a polymeric layer 330, which contains a fluorine-containing polymer (and, optionally, a drug), disposed over and in contact with the adhesion promoting layer 320. Unlike FIGS. 3A and 3B, the adhesion promoting layer 320 and the polymeric layer 330 are applied to the abluminal surface 110a of the stent substrate 110, as well as to the sides of the stent substrate 110 between the abluminal surface 110a and the luminal surface 110l, but not to the luminal surface 110l. Such a structure may be created, for example, by masking the inner luminal surface of the stent 110l during respective deposition of the adhesion promoting layer 320 and the polymeric layer 330, by removing deposited material from the inner luminal surface of the stent 110l after respective deposition of the adhesion promoting layer 320 and the polymeric drug release layer 330, or by any other suitable methodology.

The embodiments of FIGS. 3B and 3C are more demanding from an adhesion standpoint than the embodiment of FIG. 3A, because the polymeric layer 330 does not surround the stent substrate 110 as it does in FIG. 3A.

As indicated above, medical devices in accordance with the present invention contain a fluorine-containing polymer that comprises a vinylidene fluoride monomer, a hexafluoropropylene monomer, or both. One specific example of such a polymer is a poly(vinylidene fluoride) homopolymer. Another specific example of such a polymer is a poly(hexafluoropropylene) homopolymer. Another specific example of such a polymer is poly(vinylidene fluoride-co-hexafluoropropylene) (PVDF-HFP), which is a random copolymer of vinylidene fluoride and hexafluoropropylene. In preferred embodiments, the vinylidene fluoride content of PVDF-HFP ranges from 50 to 75 to 85 to 90 to 95 to 97.5 to 99 mol %, while the hexafluoropropylene content of ranges from 1 to 2.5 to 5 to 10 to 15 to 25 to 50 mol %.

As also indicated above, medical devices in accordance with the present invention contain an adhesion promoting copolymer that contains (i) at least one monomer that covalently or non-covalently bonds with the metallic substrate and (ii) at least one monomer selected from acrylate monomers, methacrylate monomers, fluorine-containing monomers, and combinations thereof.

Without wishing to be bound by theory, it is known that water has a strong propensity to "wet out" metals such as stainless steel, which frequently results in the displacement of polymeric layers that are disposed on such surfaces. However, this propensity may be combated in accordance with the invention by providing adhesion promoting polymers that form covalent or non-covalent bonds (e.g., strong acid-base interactions) with the metal surface.

More specifically, adhesion promoting copolymers are provide which include at least one type of monomer that covalently or non-covalently bonds with metallic substrate. Examples of monomers that are capable of covalently bonding to metallic substrates include those containing one or more alkoxysilane groups, for example, those containing

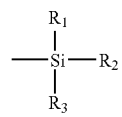

groups, for example,

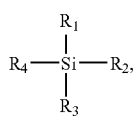

where $R_1$, $R_2$ and $R_3$ are independently alkyl groups (e.g., linear or branched $C_1$-$C_{10}$ alkyl such as methyl, ethyl, n-propyl, isopropyl, n-butyl, sec-butyl, iso-butyl, tert-butyl, n-pentyl, etc.), aryl groups (e.g., $C_6$-$C_{12}$ aryl such as phenyl, alkyl-substituted phenyl, benzyl, etc.) or alkoxy groups (e.g., linear or branched $C_1$-$C_{10}$ alkoxy such as methoxy, ethoxy, n-propoxy, isopropoxy, n-butoxy, sec-butoxy, iso-butoxy, tert-butoxy, etc.), with the proviso that at least one of $R_1$, $R_2$, $R_3$ is an alkoxy group, and where $R_4$ contains a reactive group which can be polymerized into a polymer chain or backbone (e.g., $R_4$ may be vinyl, acryloyloxy, methacryloyloxy, etc.). Such groups may be present on the monomer at the time of polymerization or may be added to a monomer within the subsequently formed polymer, with the exception of $R_4$, which is incorporated into the polymer at the time of polymerization.

Alkoxysilanes are known to react with metal hydroxides. For example, an alkoxysilane group of an adhesion promoting polymer in accordance with the invention ("Poly") may react with hydroxyl groups on metal substrate surface as schematically illustrated below:

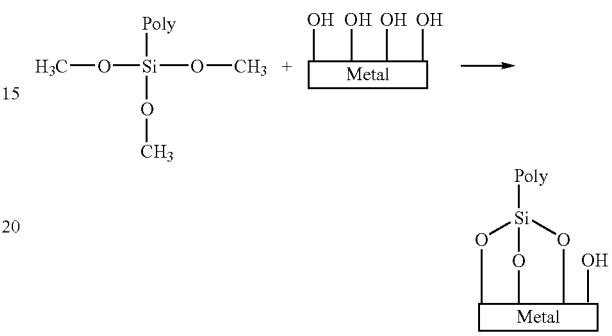

Alkoxysilane groups may also react with themselves to form Si—O—Si bonds.

Specific examples of alkoxysilane monomers include, for example, vinyl(alkylene)alkoxysilanes such as those of the formula acryloyloxy(alkylene)alkoxysilanes such as those of the formula

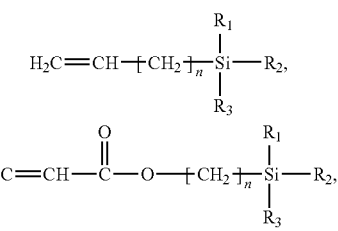

and methacryloyloxy(alkylene)alkoxysilanes such as those of the formula

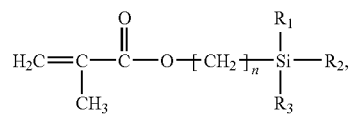

where n=0, 1, 2, 3, 4, 5, 6, 7, 8, 9, etc. and $R_1$, $R_2$ and $R_3$ are defined above, among others. More specific examples of such monomers include vinyltrimethoxysilane, vinyltriethoxysilane, vinyltriisopropoxysilane, vinylmethylenetrimethoxysilane, vinyldimethylenetrimethoxysilane, vinyltrimethylenetrimethoxysilane, (meth)acryloyloxytrimethoxysilane, (meth)acryloyloxytriethoxysilane, (meth)acryloyloxytriisopropoxysilane, (meth)acryloyloxymethylenetrimethoxysilane, (meth)acryloyloxydimethylenetrimethoxysilane, and (meth)acryloyloxytrimethylenetrimethoxysilane, among many others.

Examples of monomers that are capable of forming strong non-covalent bonds with metallic substrates include monomers with acidic groups, for example, groups that act as Bronsted acids and/or groups that act as Lewis acids. Such groups may be present on the monomers at the time of polymerization, or they may be added to monomers within a previously created polymer.

A Bronsted acid is a proton (e.g., hydrogen ion) donor, whereas a Bronsted base is a proton acceptor. A Lewis acid is an electron pair acceptor, whereas a Lewis base is an electron pair donor. Bronsted acids are Lewis acids, but the converse is not always true. Also, Bronsted bases are Lewis bases, although the converse is not necessarily true.

Without wishing to be bound by theory, it is believed that because metallic surfaces are typically basic in nature, polymers with acidic groups are able to form strong acid-base interactions with metallic surfaces. For example, an acid-base reaction can occur upon exposure of metallic surfaces to an acid. For instance, a proton may be transferred from an acidic monomer to a metal oxide at the metallic surface, or a metal oxide at the metallic surface may donate an electron pair to an acidic monomer, among other possibilities.

Specific examples of acidic monomers are those that contain Bronsted acid groups such as carboxylic acid groups (—COOH), carboxylic acid anhydride groups

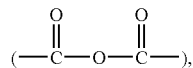

hydroxyacid groups, for example, hydroxyaromatic groups such as mono- and di-hydroxyphenyl groups, sulfonic acid groups (—$SO_3H$), and phosphonic acid groups (—$PO(OH)_2$), among others.

More specific examples of acidic monomers include acrylic acid, methacrylic acid, 2-ethylacrylic acid, 2-propylacrylic acid, 2-(bromomethyl)acrylic acid, 2-(trifluoromethyl)acrylic acid, 2-bromoacrylic acid, 2-(trifluoromethyl)acrylic acid, 2-ethylacrylic acid, methylenemalonic acid, vinylacetic acid, allylacetic acid, styryl acetic acid, 4-vinylbenzoic acid, dimethylacrylic acid, phenylacrylic acid, hydroxystyrene, dihydroxystyrene, maleic anhydride, succinic anhydride, vinylsulfonic acid, 4-styrenesulfonic acid, 3-(vinyloxy)propane-1-sulfonic acid, 2-acrylamido-2-methyl-1-propanesulfonic acid, 3-allyloxy-2-hydroxy-1-propanesulfonic acid, 2-sulfoethyl methacrylate, 2-sulfoethyl acrylate, 3-sulfopropyl acrylate, sulfoethyl methacrylamide, vinylphosphonic acid, and allylphosphonic acid, among others.

As indicated above, in addition at least one type of monomer that covalently or non-covalently bonds with metallic substrates, the adhesion promoting copolymers of the invention contain at least one type of monomer selected from acrylate monomers, methacrylate monomers, fluorine-containing monomers, and combinations thereof.

Examples of fluorine-containing monomers include vinylidene fluoride, hexafluoropropylene, tetrafluoroethylene, vinyl fluoride, 4-fluorostyrene, vinyl trifluoroacetate, and 2,2,2-trifluoroethyl acrylate.

Examples of acrylate and methacrylate monomers include low Tg acrylate monomers, low Tg methacrylate monomers, high Tg acrylate monomers, and high Tg methacrylate monomers.

As used herein, a "low Tg" monomer is a monomer that, when in homopolymer form, displays a Tg (glass transition temperature) that is below body temperature, more typically from 35° C. to 20° C. to 0° C. to −25° C. to −50° C. or below. A "high Tg" monomer is a monomer that, when in homopolymer form, displays a Tg that is above body temperature, more typically from 40° C. to 50° C. to 75° C. to 100° C. or above. Glass transition temperature may be measured, for example, by differential scanning calorimetry (DSC).

Specific examples of low Tg acrylate and methacrylate monomers (listed along with published Tg's for homopolymers of the same) are as follows: (1) low Tg acrylate monomers including: (a) alkyl acrylate monomers such as methyl acrylate (Tg 10° C.), ethyl acrylate (Tg −24° C.), propyl acrylate, isopropyl acrylate (Tg −11° C., isotactic), n-butyl acrylate (Tg −54° C.), sec-butyl acrylate (Tg −26° C.), isobutyl acrylate (Tg −24° C.), cyclohexyl acrylate (Tg 19° C.), 2-ethylhexyl acrylate (Tg −50° C.) and dodecyl acrylate (Tg −3° C.), (b) arylalkyl acrylate monomers such as benzyl acrylate (Tg 6° C.), (c) alkoxyalkyl acrylates such as 2-ethoxyethyl acrylate (Tg −50° C.) and 2-methoxyethyl acrylate (Tg −50° C.), (d) halo-alkyl acrylate monomers such as 2,2,2-trifluoroethyl acrylate (Tg −10° C.) and (e) cyano-alkyl acrylate monomers such as 2-cyanoethyl acrylate (Tg 4° C.) and (2) low Tg methacrylate monomers including (a) alkyl methacrylate monomers such as butyl methacrylate (Tg 20° C.), hexyl methacrylate (Tg −5° C.), 2-ethylhexyl methacrylate (Tg −10° C.), octyl methacrylate (Tg −20° C.), dodecyl methacrylate (Tg −65° C.), hexadecyl methacrylate (Tg 15° C.) and octadecyl methacrylate (Tg −100° C.) and (b) aminoalkyl methacrylate monomers such as diethylaminoethyl methacrylate (Tg 20° C.).

Specific examples of high Tg acrylate and methacrylate monomers (listed along with published Tg's for homopolymers of the same) are as follows: (1) high Tg acrylate monomers including alkyl acrylate monomers, such as tert-butyl acrylate (Tg 43-107° C.) and hexyl acrylate (Tg 57° C.), and isobornyl acrylate (Tg 94° C.) and (2) high Tg methacrylate monomers including (a) alkyl methacrylate monomers such as methyl methacrylate (Tg 105-120° C.), ethyl methacrylate (Tg 65° C.), isopropyl methacrylate (Tg 81° C.), isobutyl methacrylate (Tg 53° C.), t-butyl methacrylate (Tg 118° C.) and cyclohexyl methacrylate (Tg 92° C.), (b) aromatic methacrylate monomers such as phenyl methacrylate (Tg 110° C.) and including aromatic alkyl methacrylate monomers such as benzyl methacrylate (Tg 54° C.), (c) hydroxyalkyl methacrylate monomers such as 2-hydroxyethyl methacrylate (Tg 57° C.) and 2-hydroxypropyl methacrylate (Tg 76° C.) and (d) additional methacrylate monomers including isobornyl methacrylate (Tg 110° C.) and trimethylsilyl methacrylate (Tg 68° C.).

As will be appreciated by those of ordinary skill in the art, the copolymers employed in accordance with the present invention, including various fluorine-containing polymers and adhesion promoting copolymers, may be synthesized according to known methods, including cationic, anionic, and radical polymerization methods, particularly controlled/"living" cationic, anionic and radical polymerizations, among other techniques.

Living free radical polymerizations (also called controlled free radical polymerizations) may be employed in various embodiments, due to the undemanding nature of radical polymerizations in combination with the power to control polydispersities, architectures, and molecular weights that living processes provide. Monomers capable of free radical polymerization vary widely and may be selected from the following, among many others: vinyl aromatic monomers such as substituted and unsubstituted styrene, diene monomers such as 1,3-butadiene, chloroprene, and isoprene, acrylate monomers, for example, acrylate esters such as butyl acrylate and methyl acrylate, methacrylate monomers, for example, methacrylic esters such as methyl methacrylate, beta-hydroxyethyl methacrylate, and beta-dimethylaminoethyl methacrylate, as well as other unsaturated monomers including acrylic acid, acrylamide, acrylonitrile, ethylene, propylene, tetrafluoroethylene, triflourochloroethylene, iraconic acid, fumaric acid, maleic acid, methacrylic acid, methacrylonitrile, vinyl esters such as vinyl acetate, vinyl chloride, vinyl fluoride, N-vinylpyrrolidinone, N-vinylimidazole, vinylidene chloride and vinylidene fluoride.

Specific examples of free radical polymerization processes include metal-catalyzed atom transfer radical polymerization (ATRP), stable free-radical polymerization (SFRP), including nitroxide-mediated processes (NMP), and degenerative transfer including reversible addition-fragmentation chain transfer (RAFT) processes. These methods are well-detailed in the literature and are described, for example, in an article by Pyun and Matyjaszewski, "Synthesis of Nanocomposite Organic/Inorganic Hybrid Materials Using Controlled/"Living" Radical Polymerization," *Chem. Mater.*, 13:3436-3448 (2001), B. Reeves, "Recent Advances in Living Free Radical Polymerization," Nov. 20, 2001. University of Florida, T. Kowalewski et al., "Complex nanostructured materials from segmented copolymers prepared by ATRP," *Eur. Phys. J. E*, 10, 5-16 (2003).

As noted above, polymeric layers in accordance with the present invention can optionally further contain at least one drug. "Drugs," "therapeutic agents," "pharmaceutically active agents," "pharmaceutically active materials," "active pharmaceutical ingredients" (API's) and other related terms may be used interchangeably herein.

In certain embodiments, the drug may be selected from anti-restenotic agents, anti-proliferative agents, endothelial cell growth promoters, antithrombotic agents, antimicrobial agents, analgesic agents, anti-inflammatory agents, and combinations thereof, among others.

A few specific examples of drugs include taxanes such as paclitaxel (including particulate forms thereof, for instance, protein-bound paclitaxel particles such as albumin-bound paclitaxel nanoparticles, e.g., ABRAXANE), olimus family drugs such as sirolimus, everolimus, tacrolimus, biolimus and zotarolimus, Epo D, dexamethasone, heparin, estradiol, halofuginone, cilostazole, geldanamycin, alagebrium chloride (ALT-711), ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, Serca 2 gene/protein, imiquimod, human apolioproteins (e.g., AI-AV), growth factors (e.g., VEGF-2), as well derivatives of the forgoing, among others.

A wide range of drug loadings may be used in conjunction with the medical devices of the present invention. Typical loadings range, for example, from 1 wt % or less (down to 0 wt %) to 2 wt % to 5 wt % to 10 wt % to 25 wt % or more of a given polymeric layer.

Numerous techniques are available for forming polymeric layers in accordance with the present invention.

For example, where a layer is formed from one or more polymers having thermoplastic characteristics, a variety of standard thermoplastic processing techniques may be used. Using these techniques, a layer can be formed, for instance, by (a) first providing a melt that contains polymer(s) as well as any optional non-polymeric agents such as drugs and (b) subsequently cooling the melt.

Other processing techniques which may be used to form polymeric layers include solvent-based techniques. Using these techniques, a polymeric layer can be formed, for instance, by (a) first providing a solution or dispersion that contains (i) solvent, (ii) polymer(s) and (iii) any optional non-polymeric agents such as drugs and (b) subsequently removing the solvent. The solvent that is ultimately selected will contain one or more solvent species, which are generally selected based on their ability to dissolve or disperse the various species making up the layer (e.g., one or more polymers, one or more optional non-polymeric agents, etc.), in addition to other factors, including drying rate, surface tension, etc.

Preferred thermoplastic and solvent-based techniques include, for example, spraying techniques, dipping techniques, spin coating techniques, web coating techniques, meniscus coating techniques, gravure or other transfer coating techniques (e.g., knife or blade coating, brush coating, roll coating, ink jet coating, etc.), extrusion techniques, techniques involving coating via mechanical suspension including air suspension, electrostatic techniques, and combinations of these processes.

A specific embodiment of the invention will now be described in the Example to follow. This Example should not be construed as limiting. Other examples can be envisioned by those of ordinary skill in the art.

EXAMPLE

PVDF-HFP with an 85:15 monomer ratio was obtained from Solvay.

Poly(n-butyl methacrylate)(PBMA) was obtained from Esschem, Linwood, Pa., USA.

A random adhesion promoting copolymer, poly(methyl methacrylate-co-n-butyl methacrylate-co-acrylic acid) (MMA/BA/AA copolymer) was formed by free radical polymerization. More particularly, a copolymer containing MMA, BA and AA in the following weight ratios: 49/46/5 MMA/BA/AA (theoretical Tg=10° C.) was synthesized by free radical polymerization in refluxing toluene using benzoyl peroxide as the initiator. The monomers and initiator were combined and slowly added (over 3 hr) to refluxing toluene under a nitrogen atmosphere. After addition of the monomers and initiator, the reaction was allowed to proceed for an additional 3 hrs. The polymer solution was precipitated into heptane, filtered and dried under vacuum.

A 10% wt % solution of the MMA/BA/AA copolymer in THF was knife coated onto stainless steel foil and dried at 70° C. to form an adhesion promoting layer in accordance with the invention. Layer thickness was <1 µm.

A 10 wt % solution of the PBMA in THF was knife coated onto stainless steel foil and dried at 70° C. to form a comparative adhesion promoting layer. Layer thickness was <1 µm.

25% wt % PVDF-HFP in 70/30 wt/wt acetone/cyclohexanone was knife coated onto bare stainless steel foil or stainless steel foil with an adhesion promoting layer prepared as described above. The coated foil was dried at 70° C. for 1 hr in a convection oven followed by 24 h at 70° C. under vacuum. The dry coating thickness was about 60 µm.

Adhesion was determined by peeling the PVDF-HFP coating from the foil (180° peel angle) utilizing a tensile tester. In samples employing an adhesion promoting layer, the PVDF-HFP is coated beyond the adhesion promoting layer, so that at least a portion of the PVDF-HFP coating is deposited directly onto the stainless steel, to which it has poor adhesion. This allows one to readily start the peel process from the stainless steel. Where an adhesion promoting layer is provided, during the peel test, the peel front reaches the adhesion promoting layer, at which point one measures the adhesion-promoting capability of the layer. Dry adhesion was performed in air. Wet adhesion was determined after incubation of the coated samples in phosphate buffered saline (PBS) with Tween surfactant (pH 7.4, 0.05% wt/vol Tween 20) at 37° C. for 4 days. The samples were removed from the incubation bath and transferred to a water bath. 180 degree peel adhesion of the submersed samples was then measured.

Peel adhesion as measured by the tensile tester is shown in the following Table 1. PVDF-HFP has almost no measurable adhesion to stainless steel.

The use of the PBMA adhesion promoting layer resulted in very good dry adhesion but wet adhesion is essentially zero. This is not critical in the case of a conformally coated medical device (see, e.g., the coated stent strut of FIG. 3A), where coating integrity is maintained by the mechanical cohesive properties of the polymeric coating layer. However, where a medical device is not completely coated (see, e.g., the coated stent strut of FIGS. 3B and 3C), good wet adhesion is essential.

Like PBMA, the MMA/BA/AA copolymer adhesion promoting layer has good dry adhesion. Unlike PBMA, the MMA/BA/AA copolymer has good wet adhesion as well.

TABLE 1

180 Degree Peel Adhesion Results

| Top Coat | Adhesion Primer | Dry Adhesion | Wet Adhesion |
| --- | --- | --- | --- |
| PVDF-HFP | NONE | 3 g/in | — |
| PVDF-HFP | PBMA (control) | 1373 g/in | 0 g/in |
| PVDF-HFP | 49/46/5 MMA/BA/AA | >1831 g/in | 1020 g/in |

In previous studies, it was found that AA provides good adhesion to metals such as stainless steel when included in a MMA/BA/AA copolymer in low amounts such as those employed here. As the amount of AA increases, however, wet adhesion ultimately begins to decline. Also, swelling can occur in water at higher amounts of AA, with the copolymer eventually becoming water dispersible. An increase in AA can also result in a concurrent decrease in solubility of the adhesion promoting copolymer in organic solutions. For further details see U.S. Ser. No. 11/803,433 to Kangas.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A medical device comprising: a metallic substrate and a polymeric region disposed over and in contact with the metallic substrate, said polymeric region comprising (1) a fluorine-containing polymer which is a random copolymer of vinylidene fluoride and hexafluoropropylene and (2) an adhesion promoting copolymer that comprises (i) a first monomer which is an acidic monomer that non-covalently bonds with the metallic substrate and (ii) n-butyl acrylate as a second monomer.

2. The medical device of claim 1, wherein said medical device is an implantable or insertable medical device.

3. The medical device of claim 1, wherein said substrate is a metallic stent.

4. The medical device of claim 1, wherein said substrate is a metallic stent and wherein the polymeric region covers an outer abluminal surface of the stent, but not an inner luminal surface of the stent.

5. The medical device of claim 1, wherein said metallic substrate is selected from the group consisting of a stainless steel substrate, a platinum enriched stainless steel substrate, a nitinol substrate, and a substrate comprising cobalt and chromium.

6. The medical device of claim 1, wherein the first monomer comprises an acidic group selected from the group consisting of a carboxylic acid group, a carboxylic acid anhydride group, a hydroxyl acid group, a sulfonic acid group, a phosphonic acid group and combinations thereof.

7. The medical device of claim 6, wherein said first monomer is selected from the group consisting of an acrylic acid monomer, a methacrylic acid monomer, a maleic acid monomer, a maleic anhydride monomer, and combinations thereof.

8. The medical device of claim 1, wherein said adhesion promoting copolymer further comprises a methyl methacrylate monomer.

9. The medical device of claim 1, wherein said polymeric region comprises a polymeric layer disposed over and in contact with said metallic substrate, said polymeric layer comprising said fluorine-containing polymer and said adhesion promoting copolymer.

10. The medical device of claim 1, wherein said polymeric region comprises (a) an adhesion promoting layer comprising said adhesion promoting copolymer disposed over and in contact with said metallic substrate, and (b) a polymeric layer comprising said fluorine-containing polymer disposed over and in contact with said adhesion promoting layer.

11. The medical device of claim 1, wherein said polymeric region further comprises a drug.

12. The medical device of claim 11, wherein said drug is selected from the group consisting of antiproliferative agents, anti-restenotic agents, antithrombotic agents, endothelial cell growth promoters, antimicrobial agents, analgesic agents, and anti-inflammatory agents.

13. The medical device of claim 1, wherein said first monomer comprises a carboxylic acid group.

14. The medical device of claim 1, wherein said first monomer is selected from the group consisting of an acrylic acid monomer, a methacrylic acid monomer, a maleic acid monomer, and combinations thereof.

15. The medical device of claim 1, wherein said adhesion promoting copolymer further comprises an alkyl methacrylate monomer.

16. A medical device comprising: a metallic substrate and a polymeric region disposed over and in contact with the metallic substrate, said polymeric region comprising (a) an adhesion promoting copolymer that comprises an acrylic acid monomer as a first monomer and a second monomer selected from the group consisting of alkyl acrylate monomers, alkyl methacrylate monomers, and combinations thereof, and (b) a fluorine-containing polymer that comprises a combination of vinylidene fluoride monomer and hexafluoropropylene monomer.

17. The medical device of claim 16, wherein said second monomer is an n-butyl acrylate monomer.

18. The medical device of claim 16, wherein said second monomer is a combination of an n-butyl acrylate monomer and a methyl methacrylate monomer.

19. The medical device of claim 18, wherein said device is not completely coated with said polymeric region.

20. The medical device of claim 16, wherein said second monomer is an alkyl methacrylate monomer-.

21. The medical device of claim 16, wherein said second monomer is a methyl methacrylate monomer.

22. The medical device of claim 16, wherein said second monomer is a combination of an alkyl acrylate monomer and an alkyl methacrylate monomer.

23. A medical device comprising: a metallic substrate and a polymeric region disposed over and in contact with the metallic substrate, said polymeric region comprising (1) a fluorine-containing polymer which is a random copolymer of vinylidene fluoride and hexafluoropropylene and (2) an adhesion promoting copolymer that comprises (i) an acidic monomer that non-covalently bonds with the metallic substrate and (ii) an alkyl methacrylate monomer.

24. The medical device of claim 23, wherein said alkyl methacrylate monomer is methyl methacrylate monomer.

25. The medical device of claim 23, wherein said adhesion promoting copolymer further comprises an alkyl acrylate monomer.

* * * * *